(12) United States Patent
Li et al.

(10) Patent No.: US 10,375,318 B2
(45) Date of Patent: Aug. 6, 2019

(54) APPARATUSES AND METHODS FOR OPTICAL CALIBRATION

(71) Applicants: Xuesong Li, Fushun (CN); Siyi Dai, Fushun (CN)

(72) Inventors: Xuesong Li, Fushun (CN); Siyi Dai, Fushun (CN)

( * ) Notice: Subject to any disclaimer, the term of this patent is extended or adjusted under 35 U.S.C. 154(b) by 14 days.

(21) Appl. No.: 15/696,791

(22) Filed: Sep. 6, 2017

(65) Prior Publication Data

US 2019/0075248 A1    Mar. 7, 2019

(51) Int. Cl.
*G01N 21/64* (2006.01)
*H04N 5/247* (2006.01)
*G06F 17/50* (2006.01)
*H04N 5/225* (2006.01)

(52) U.S. Cl.
CPC ......... *H04N 5/247* (2013.01); *G06F 17/5009* (2013.01); *H04N 5/2256* (2013.01)

(58) Field of Classification Search
CPC ...... G09B 9/00; G01N 21/64; G01N 21/6458; G01N 2201/127; H04N 5/247; H04N 5/225; G06F 17/50
See application file for complete search history.

(56) References Cited

U.S. PATENT DOCUMENTS

| | | | | |
|---|---|---|---|---|
| 5,561,290 A | * | 10/1996 | Strobel | G01J 1/02 250/252.1 |
| 8,602,610 B1 | * | 12/2013 | Lauer | F21S 6/001 362/392 |
| 2011/0286636 A1 | * | 11/2011 | Purcell | G01N 21/25 382/110 |
| 2013/0126757 A1 | * | 5/2013 | Sywe | G01N 21/64 250/459.1 |
| 2013/0189658 A1 | * | 7/2013 | Peters | G09B 5/00 434/234 |
| 2015/0248845 A1 | * | 9/2015 | Postlethwaite | G09B 19/24 434/234 |
| 2016/0166862 A1 | * | 6/2016 | Qui | A62C 3/025 169/24 |
| 2017/0268948 A1 | * | 9/2017 | List | G01L 5/13 |

* cited by examiner

*Primary Examiner* — Alison Slater
(74) *Attorney, Agent, or Firm* — Ude Lu; Cozen O'Connor (57) ABSTRACT

An apparatus for optical calibration includes a calibration target simulating a combustion. The calibration target further includes a first light-emitting pattern and a first light-emitting mechanism effecting the first light-emitting pattern. The apparatus includes two optical cameras aiming at the calibration target, wherein each optical camera has an observation axis and there is an angle between the two observation axes.

16 Claims, 7 Drawing Sheets

APPARATUSES AND METHODS FOR OPTICAL CALIBRATION

FIELD OF THE DISCLOSURE

The instant disclosure relates generally to optical calibration. More specifically, the disclosure relates to apparatuses and methods of building a calibration target configured for calibrating parameters of combustion, aerosol sprays, and/or moving particles modeling algorithms.

BACKGROUND

Fire, combustion, and explosion are molecular oxidization processes that transform chemical energies to other forms of energies, e.g., light, sound, heat, etc.

In some applications, it is desirable to have a computerized model to simulate and characterize the process of a fire, combustion, and/or explosion. For example, in the automobile industry, engineers may be interested in knowing how gasoline combustions happen within a cylinder of an engine, wherein the cylinder may have complex internal geometries.

Observation of the light emitted by fire, combustion, or explosion can be used to build a computerized model. An important aspect to build such computerized model is to have a repeatable fire or combustion target, so that the parameters of the computerized model can be calibrated. However, it is theoretically not possible to exactly reproduce a combustion. The lack of reproducibility makes quantitative characterization of flames, combustion, or explosion difficult. Further, the lack of reproducibility makes the calibration of computerized models for predicting flame, combustion, and explosion extremely difficult, if not impossible.

The disclosure herein aims to resolve this issue by making calibration targets of flame, aerosol sprays, and/or combustion for optical calibration of computerized models.

SUMMARY

The instant disclosure relates generally to optical calibration. More specifically, the disclosure relates to apparatuses and methods of building a calibration target configured for calibrating parameters of combustion, aerosol sprays, and/or moving particles modeling algorithms.

An apparatus for optical calibration includes a calibration target simulating a combustion. The calibration target further includes a first light-emitting pattern and a first light-emitting mechanism effecting the first light-emitting pattern. The apparatus includes two optical cameras aiming at the calibration target, wherein each optical camera has an observation axis and there is an angle between the two observation axes.

An apparatus for optical calibration includes a first calibration target simulating moving particles. The first calibration target further includes a first plurality of light-emitting particles, wherein each particle has a position at a first time (T1), and a first light-emitting mechanism effecting the first plurality of light-emitting particles. The apparatus includes two optical cameras aiming at the calibration target, wherein each optical camera has an observation axis and there is an angle between the two observation axes.

A method for optical calibration includes the following steps: creating a first digital model of a combustion, wherein the first digital model includes a first parameter; fabricating a calibration target of the combustion based on the first digital model; setting up at least two image capturing devices aiming at the calibration target; performing measurements of the calibration target using the at least two image capturing devices; and constructing a second digital model based on the measurements using an algorithm, wherein the second digital model includes a second parameter.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the concepts and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed systems and methods, reference is now made to the following descriptions taken in conjunction with the accompanying drawings.

DETAILED DESCRIPTION

A "calibration target" is a physical apparatus specifically designed and manufactured to simulate a combustion and/or a process of combustion. A combustion may include, propagating flame, moving particles, sprayed particles, etc. The particles may include, e.g., fuel, ethanol, and other flammable chemical molecules. A "calibration target" is not a combustion and/or a process of combustion itself. The calibration target is specifically designed for optical calibration purposes. In some particular embodiments, the optical calibrations are further configured to calibrate computer model parameters, wherein the computer model is an algorithm that characterizes an actual combustion and/or an actual process of combustion. One purpose of using a calibration target is to provide a target for optical calibration so that the precision and accuracy in characterizing an actual combustion and a combustion process can be increased.

Figure 1:
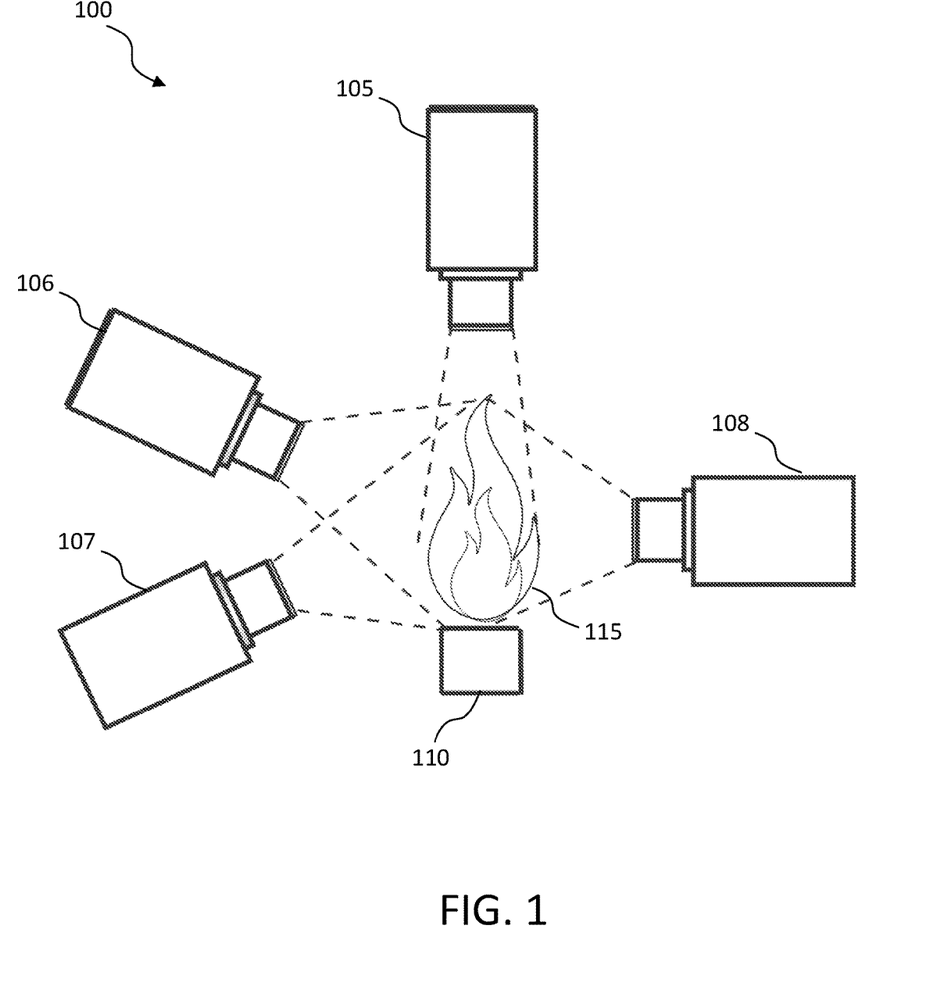
FIG. 1 shows an example of observing a combustion according to one embodiment of the disclosure.

FIG. 1 shows an example 100 of observing a combustion according to one embodiment of the disclosure. The example 100 includes four different optical cameras 105, 106, 107, 108. The example 100 further includes a source of combustion 110 and a combustion 115.

The observation axis of a camera is defined as a center line of the visual field of the camera. As shown in FIG. 1, the example includes four different optical cameras 105, 106, 107, 108. There is a 90 degree angle between the observation axis of camera 108 and the observation axis of camera 105. There is a 45 degree angle between the observation axis of camera 105 and the observation axis of camera 106. There is a 45 degree angle between the observation axis of camera 107 and the observation axis of camera 105. It is noted that the angle between any two cameras can range from 0 degrees to 180 degrees.

Each of the cameras 105, 106, 107, 108 observes the combustion 115 from a different angle. Each camera may observe the process of the combustion 115 for one or more predetermined periods of time. Each camera may take a plurality of images and/or videos during the process of the combustion 115. The images and/or videos taken by the cameras can be digital or analog, preferably digital. The observed images can be analyzed by one or more algorithms to extract useful information of the combustion 115.

In some embodiments, the cameras 105, 106, 107, 108 can be replaced by other appropriate light sensing optical and/or electrical sensors, e.g., photoconductive devices, photovoltaics, photodiodes, phototransistors, etc. Such light sensing optical and/or electrical sensors also applies to example 200, example 300, example 400, and method 700.

In one embodiment, if the combustion 115 is a fuel combustion within an engine, the useful information may include fuel injection timing, shape of fuel spraying, quantity of fuel, ignition location, ignition timing, flame propagation, fuel burning efficiency, energy transfer efficiency, etc. It is noted that the above mentioned useful information is exemplary only and are not limiting the scope of the disclosure in any way.

It is noted that, in general, more cameras produce more accurate observation results and information extracted from the observation can be more accurate. In one embodiment, the observation setting may include two cameras. In one embodiment, the observation setting may include three cameras. In one embodiment, the observation setting may include four cameras. In one embodiment, the observation setting may include five cameras. In one embodiment, the observation setting may include six cameras. In one embodiment, the observation setting may include more than six cameras.

The source of combustion 110 can be any apparatus that produces combustion in interest. In one embodiment, the source of combustion 110 can be an engine for a car, a boat, or an airplane.

Figure 2:
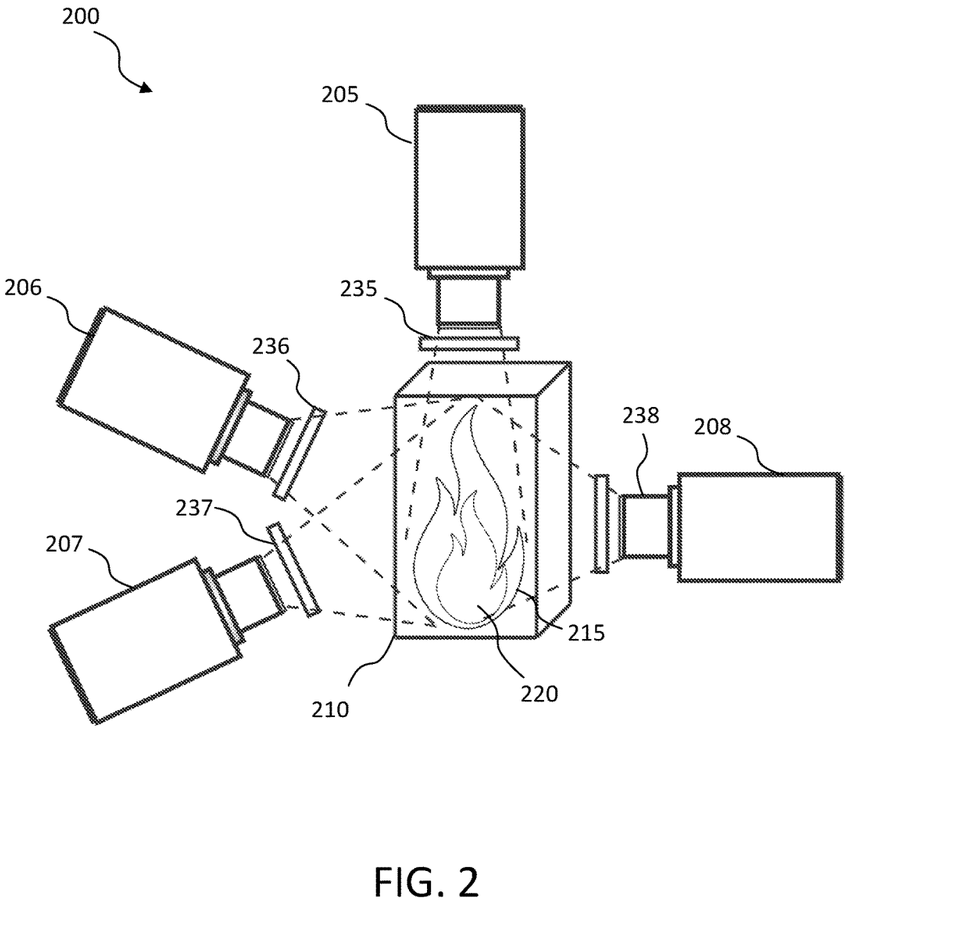
FIG. 2 shows an example of observing a calibration target of combustion according to one embodiment of the disclosure.

FIG. 2 shows an example 200 of observing a calibration target 210 of combustion according to one embodiment of the disclosure. The example 200 includes four cameras 205, 206, 207, 208. Camera 205 includes an optical filter 235. Camera 206 includes an optical filter 236. Camera 207 includes an optical filter 237. Camera 208 includes an optical filter 238. In one embodiment, the optical filter 235, 236, 237, 238 can be a filter that allows a specific wavelength of light to pass through, e.g., blue, red, green, yellow, infra-red ray, UV ray, etc. In another embodiment, the optical filter 235, 236, 237, 238 can be a filter that rejects a specific wavelength of light to pass through, e.g., blue, red, green, yellow, infra-red ray, UV ray, etc. It is noted that any kind of optical filter appropriate can be used in the embodiments of this disclosure. With the appropriate filters, the cameras may observe different portions of the calibration target 210.

The calibration target 210 includes light-emitting patterns that mimic combustions, e.g., combustion 115. The calibration target 210 may include light-emitting patterns with different intensities. It is noted that the calibration target 210 may include any type of light-emitting pattern. The light-emitting pattern may include different light-emitting intensities at different portions.

As shown in FIG. 2, the calibration target 210 includes a first light-emitting pattern 215 with a first intensity and a second light-emitting pattern 220 with a second intensity. In one embodiment, the first light-emitting pattern 215 has a light intensity higher than that of the second light-emitting pattern 220. In another embodiment, the first light-emitting pattern 215 has a light intensity lower than that of the second light-emitting pattern 220.

The calibration target 210 may include different light-emitting mechanisms. In one embodiment, the light-emitting mechanisms included in the calibration target 210 may be fluorescence. The term "fluorescence" is defined as an emission of light by a substance that has absorbed an excitation light or other excitation electromagnetic radiation. Normally, the excitation light has a shorter wavelength and higher frequency than the emitted fluorescence light. For example, in one embodiment, the excitation light is blue (shorter wavelength and higher frequency) and the emitted light is red (longer wavelength and lower frequency). If the light-emitting mechanism is fluorescence, once the excitation light ceases, the emitted light also ceases in a relatively short time frame, usually within seconds.

In one fluorescence embodiment, a single fluorescence substance with different concentration distribution can be used to create the different light-emitting patterns 215, 220. For example, to create a calibration target 210 wherein the first light-emitting pattern 215 is brighter than the second light-emitting pattern 220, the first light-emitting pattern 215 contains higher concentration of the single fluorescence substance than that of the second light-emitting pattern 220.

In another fluorescence embodiment, a plurality of fluorescence substances may be used to create the different light-emitting patterns 215, 220. For example, a first fluorescence substance that can be excited by UV ray and emits red light can be used to create the first light-emitting pattern 215. A second fluorescence substance that can be excited by UV ray and emits green light can be used to create the second light-emitting pattern 220. Different concentration distribution of the plurality of fluorescence substances can be used to create more variety of the light-emitting patterns. Appropriate optical filters 235, 236, 237, 238 can be used to observe the specific light-emitting pattern in interest. For example, an optical filter that only allows red light to pass through may be used to observe the first light-emitting pattern 215 (the first light-emitting pattern 215 contains the fluorescence substance that emits red light). In another example, an optical filter that only allows green light to pass through may be used to observe the second light-emitting pattern 220 (the second light-emitting pattern 220 contains the fluorescence substance that emits green light).

In another embodiment, the light-emitting mechanisms included in the calibration target 210 may include phosphorescence. The term "phosphorescence" is defined as an emission of light by a substance that absorbs radiation energy and emits it at a longer period of time, usually hours. The slower time scale of re-emission, compared to fluorescence, is due to forbidden energy state transitions in quantum mechanics. Everyday examples of phosphorescent materials are the glow-in-the-dark toys, stickers, paint, and clock dials that glow for some time after being charged with a bright light.

In one phosphorescence embodiment, a single phosphorescence substance with different concentration distribution can be used to create the different light-emitting patterns 215, 220. For example, to create a calibration target 210 wherein the first light-emitting pattern 215 is brighter than the second light-emitting pattern 220, the first light-emitting pattern 215 contains higher concentration of the single phosphorescence substance than that of the second light-emitting pattern 220.

In another phosphorescence embodiment, a plurality of phosphorescence substances may be used to create the different light-emitting patterns 215, 220. For example, a first phosphorescence substance that absorbs UV ray and emits red light can be used to create the first light-emitting pattern 215. A second phosphorescence substance absorbs UV ray and emits green light can be used to create the second light-emitting pattern 220. Different concentration distribution of the plurality of phosphorescence substances can be used to create more variety of the light-emitting patterns. Appropriate optical filters 235, 236, 237, 238 can be used to observe the light-emitting pattern in interest. For example, an optical filter that only allows red light to pass through may be used to observe the first light-emitting pattern 215 (the first light-emitting pattern 215 contains the phosphorescence substance that emits red light). In another example, an optical filter that only allows green light to pass through may be used to observe the second light-emitting pattern 220 (the second light-emitting pattern 220 contains the phosphorescence substance that emits green light).

In another embodiment, the light-emitting mechanisms included in the calibration target 210 may be an electricity-driven light source, such as light bulbs, light-emitting diodes (LEDs), laser diodes, solid state light sources, etc. In one embodiment, the first light-emitting pattern 215 and the second light-emitting pattern 220 can be achieved by having a single light source disposed internally in the calibration target 210, e.g., a light bulb, and patterned thickness and/or roughness of the surface material of the calibration target 210.

For example, to create a calibration target 210 wherein the first light-emitting pattern 215 is brighter than the second light-emitting pattern 220, the surface material of the first light-emitting pattern 215 is thinner than that of the second light-emitting pattern 220. In another example, to create a calibration target 210 wherein the second light-emitting pattern 220 is darker than the first light-emitting pattern 215, the surface material of the second light-emitting pattern 220 is thicker than that of the first light-emitting pattern 215.

In another embodiment, the light-emitting mechanisms of the calibration target 210 may be replaced by light-reflecting mechanisms. Light-reflecting mechanisms means patterns or particles included in the calibration target that passively reflects light, instead of actively emitting light. For example, to differentiate light-reflecting mechanisms from light-emitting mechanisms, fluorescence, phosphorescence, the electricity-driven light source are considered light-emitting mechanisms, not light-reflecting mechanisms in this disclosure.

For clarity purposes, light-emitting patterns 215, 220 will be referred to as light-reflecting patterns in this paragraph. In one embodiment, the first light-reflecting pattern 215 may be effected by disposing the right amount of a first kind of metal particles at the appropriate positions. The first metal particles may have a first reflection rate. The second light-reflecting pattern 220 can be effected by disposing the right amount of a second kind of metal particles at the appropriate positions. For example, if a brighter first light-reflecting pattern 215 is desired, a material with a higher light reflecting rate can be chosen, e.g. silver (Ag). If a darker second light-reflecting pattern 220 is desired, a material with a lower light reflecting rate can be chosen, e.g. copper (Cu). Or, in another embodiment, a same material, e.g., Cu or Ag, can be used at different concentration to create different light-reflecting intensities for different patterns. The above mentioned examples and materials are exemplary only and are not limiting the scope of the disclosure in anyway. The principle of light-reflecting mechanisms and patterns also apply to example 400, apparatus 500, and method 700.

As shown in FIG. 2, there is a 90 degree angle between the observation axis of camera 208 and the observation axis of camera 205. There is a 45 degree angle between the observation axis of camera 205 and the observation axis of camera 206. There is a 45 degree angle between the observation axis of camera 207 and the observation axis of camera 205. It is noted that the angle between any two cameras can range from 0 degrees to 180 degrees.

The calibration target 210 of FIG. 2 is predesigned. The parameters of the light-emitting patterns 215, 220 are known from a mathematical modeling standpoint. The actual images captured by the cameras 205, 206, 207, 208 can be used to verify and calibrate the parameters of a mathematical model configured to model a combustion 115, so that the calibrated model can be used more accurately.

Figure 3:
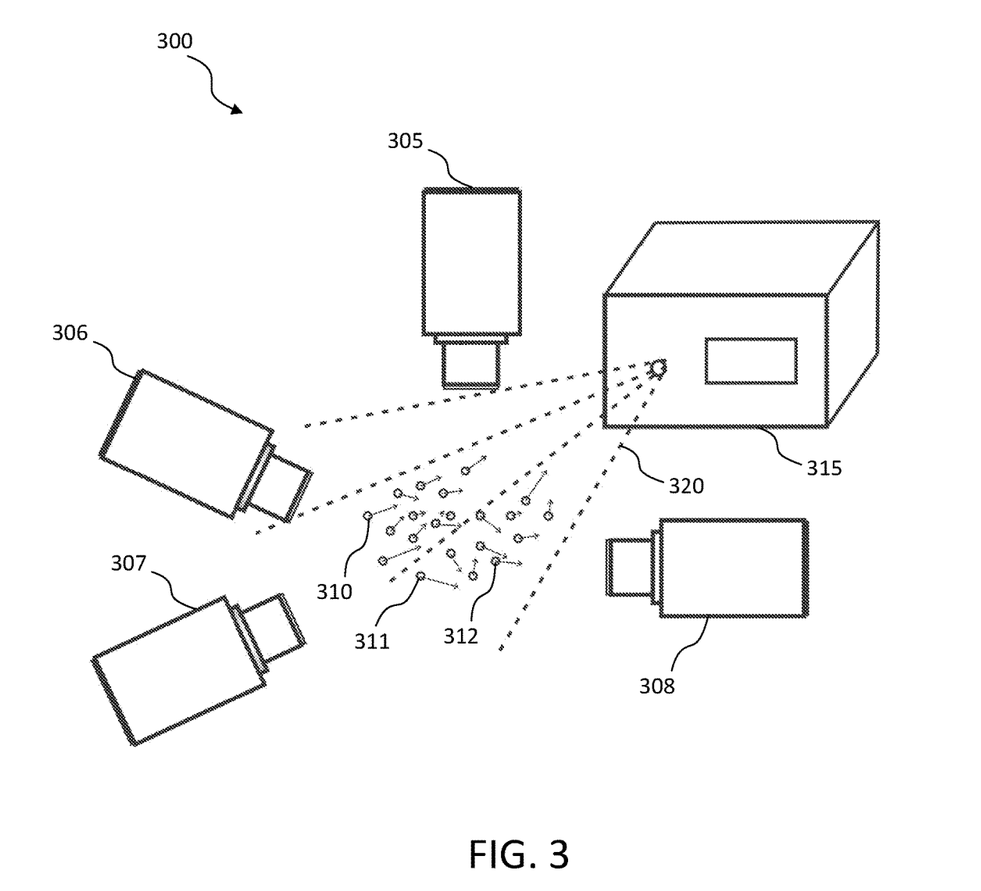
FIG. 3 shows an example of observing moving particles according to one embodiment of the disclosure.

FIG. 3 shows an example 300 of observing moving particles 310, 311, 312 according to one embodiment of the disclosure. The example 300 includes four cameras 305, 306, 307, 308. The example 300 further includes a light source 315. The light source emits light 320. The moving particles 310, 311, 312 are being illuminated by the light 320 and observed by the cameras 305, 306, 307, 308.

As shown in FIG. 3, the example 300 includes four different optical cameras 305, 306, 307, 308. There is a 90 degree angle between the observation axis of camera 308 and the observation axis of camera 305. There is a 45 degree angle between the observation axis of camera 305 and the observation axis of camera 306. There is a 45 degree angle between the observation axis of camera 307 and the observation axis of camera 305. It is noted that the angle between any two cameras can range from 0 degrees to 180 degrees.

Each of the cameras 305, 306, 307, 308 observe the individual trajectories of the moving particles 310, 311, 312 from different angles. Each camera may observe the individual trajectories of the moving particles 310, 311, 312 for a predetermined period of time. Each camera may take a plurality of images and/or videos of the motions of the moving particles 310, 311, 312. The images and/or videos taken by the cameras can be digital or analog, preferably digital. The observed images can be analyzed by one or more algorithms to extract useful information.

In one embodiment, the moving particles 310, 311, 312 can be light-emitting, e.g., fluorescence or phosphorescence substances. In another embodiment, the moving particles 310, 311, 312 can be non-light-emitting.

In one embodiment, the moving particles 310, 311, 312 are fuel particles being sprayed into a piston cylinder, chamber, tube, etc. The fuel particles may then be ignited to create a combustion, e.g., combustion 115. The cameras 305, 306, 307, 308 observe the individual trajectories of the moving particles 310, 311, 312 from different angles as well as the combustion process.

In one embodiment, if the moving particles 310, 311, 312 are fuel particles, the useful information observed by the cameras 305, 306, 307, 308 may include shape of fuel spraying, efficiency of the mixing of fuel particles, quantity of fuel injection, ignition location, ignition timing, flame propagation, fuel burning efficiency, energy transfer efficiency, etc. It is noted that the above mentioned useful information is exemplary only and are not limiting the scope of the disclosure in any way.

It is noted that, in general, more cameras produce more accurate observation results and information extracted can be more accurate. In one embodiment, the observation setting may include two cameras. In one embodiment, the observation setting may include three cameras. In one embodiment, the observation setting may include four cameras. In one embodiment, the observation setting may include five cameras. In one embodiment, the observation setting may include six cameras. In one embodiment, the observation setting may include more than six cameras.

It is also noted that, for some applications, the moving particles 310, 311, 312 can be static. In such applications, the moving particles 310, 311, 312 shall be referred to as static particles 310, 311, 312. Static particles are defined as particles being motionless during the period of time of observation. Static particles can be created by different mechanisms, e.g., low temperature, doping in gel or solid state material, etc.

Figure 4:
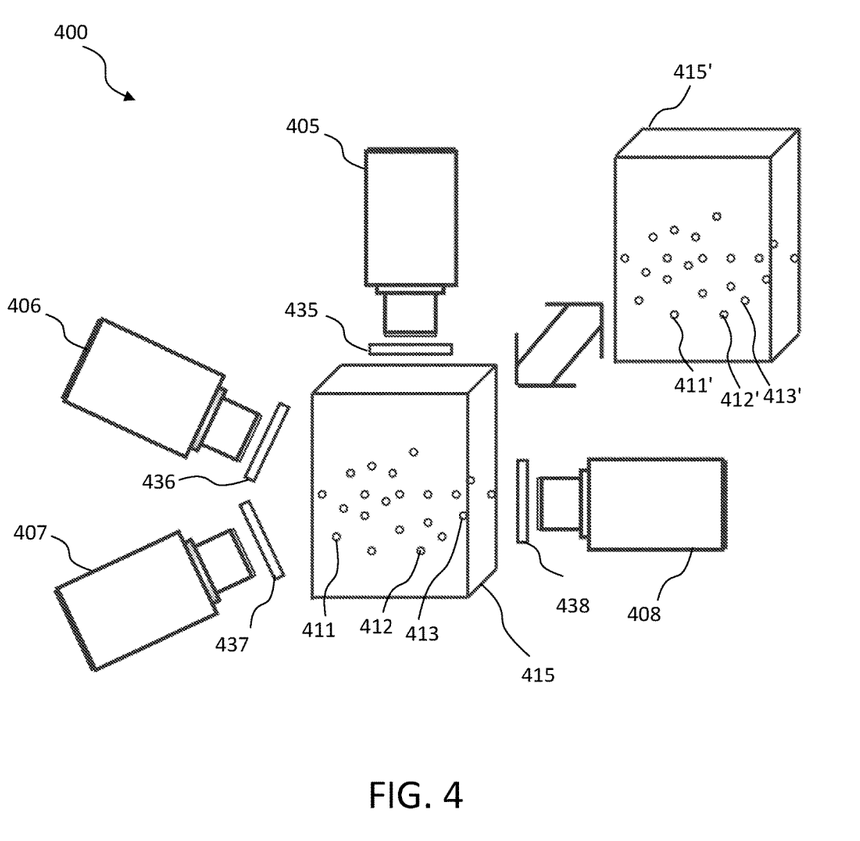
FIG. 4 shows an example of observing a calibration target of moving particles according to one embodiment of the disclosure.

FIG. 4 shows an example 400 of observing a calibration target 415 of moving particles 411, 412, 413 according to one embodiment of the disclosure. The calibration target 415' includes the same moving particles 411', 412', 413', but at a later time point than the calibration target 415. The calibration targets 415 and 415' are two physically separate calibration targets. The example 400 includes four cameras 405, 406, 407, 408.

The example 400 includes two calibration targets 415 and 415'. The calibration target 415 includes moving particles 411, 412, 413 at positions at time T1. The calibration target 415' includes moving particles 411', 412', 413' at positions at time T2, wherein T2 is later than T1. For example, T1 can be at X ms, and T2 can be at X+5 ms, wherein X can be any number. It is noted that embodiments similar to example 400 can include a plurality of calibration targets representing particles at different timings. There is no limitation as to how many calibration targets can be used, or what time intervals are among the calibration targets. In general, more calibration targets representing different time points can result in more accurate calibration of the algorithms.

Camera 405 includes an optical filter 435. Camera 406 includes an optical filter 436. Camera 407 includes an optical filter 437. Camera 408 includes an optical filter 438. In one embodiment, the optical filter 435, 436, 437, 438 can be a filter that allows specific bandwidth of light to pass through, e.g., blue, red, green, yellow, infra-red ray, UV ray, etc. In another embodiment, the optical filter 435, 436, 437, 438 can be a filter that rejects a specific bandwidth of light to pass through, e.g., blue, red, green, yellow, infra-red ray, UV ray, etc. With the appropriate filters, the cameras may observe different portions of the calibration target 410.

The moving particles 411, 412, 413 may emit light. In one embodiment, the moving particles 411, 412, 413 may be fluorescence substances. In one embodiment, the moving particles 411, 412, 413 may be phosphorescence substances. In another embodiment, the calibration target 415 may include an electricity-driven internal light source (e.g., light bulb, LED, etc), and the moving particles 411, 412, 413 have a thinner surface material compared to the surrounding areas, so that more light can pass through the surface of the moving particles 411, 412, and 413 than the surrounding areas.

The moving particles 411', 412', 413' may emit light. In one embodiment, the moving particles 411', 412', 413' may be fluorescence substances. In one embodiment, the moving particles 411', 412', 413' may be phosphorescence substances. In another embodiment, the calibration target 415' may include an electricity-driven internal light source (e.g., light bulb, LED, etc.), and the moving particles 411', 412', 413' have a thinner surface material compared to the surrounding areas, so that more light can pass through the surface of the moving particles 411', 412', and 413'.

Because the positions and the timings of the moving particles 411, 411', 412, 412', 413, 413' are known, the moving directions, the trajectories, the moving speeds of each of the particles can be calculated and be used to calibrate the algorithm and/or computer model that is used to model the moving particles 310, 311, 312.

In other embodiments, it is appropriate to include only one calibration target 415 for the purpose to simulate static particles, e.g., static particles 310, 311, 312.

Figure 5:
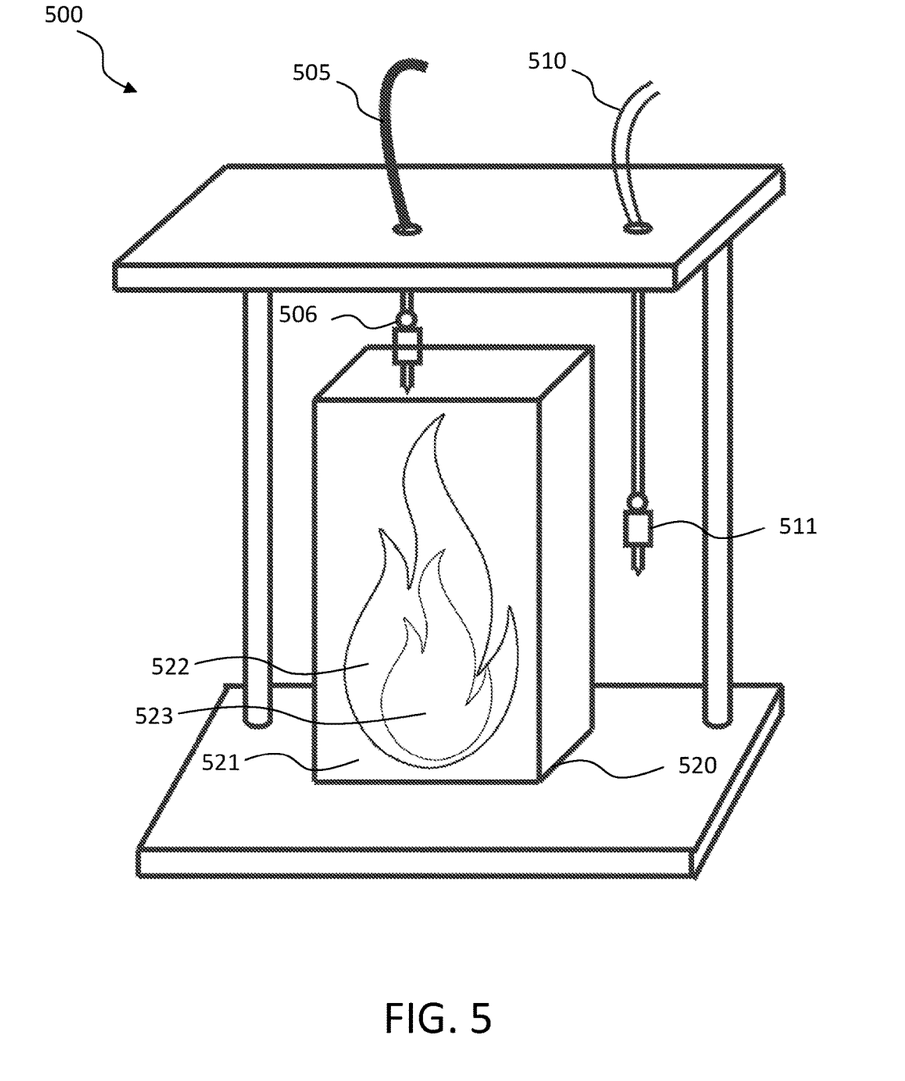
FIG. 5 shows an apparatus that fabricates a calibration target according to one embodiment of the disclosure.

FIG. 5 shows an apparatus 500 that fabricates a calibration target 520 according to one embodiment of the disclosure. The apparatus 500 includes a first feeding line 505 and a first ejector 506. The apparatus 500 includes a second feeding line 510 and a second ejector 511. In one embodiment, the apparatus 500 can be a 3D printer.

In one embodiment, the first feeding line 505 feeds the first ejector 506 with a light-emitting substance, e.g., fluorescence, phosphorescence, etc. The second feeding line 510 feeds the second ejector 511 with substances that do not have any light-emitting capability. Each ejector 506, 511 can freely move within a space to spray the substances at an appropriate location with an appropriate concentration. It is noted that there is no limitation as to how many feed lines or ejectors the apparatus 500 can have.

In one embodiment, the first light-emitting pattern 521 has a first light-emitting intensity. The second light-emitting pattern 522 has a second light-emitting intensity that is brighter than the first intensity. The third light-emitting pattern 523 has a third light-emitting intensity that is brighter than the second intensity. In such, the second light-emitting pattern 522 contains higher concentration of light-emitting substances than the first light-emitting pattern 521; the third light-emitting pattern 523 contains higher concentration of light-emitting substances than the second light-emitting pattern 522.

In one embodiment, the calibration target 520 includes an internal light source, such as a light bulb, light-emitting diodes (LEDs), laser diodes, solid state light source, etc. In one embodiment, the first 521, the second 522, and the third 523 light-emitting patterns can be achieved by having different thickness and/or roughness of the surface material, wherein brighter light-emitting pattern is achieved by having thinner surface material. In such an embodiment, only one ejector 506 or 511 with a single substance may be used to achieve a functional calibration target 520.

Figure 6:
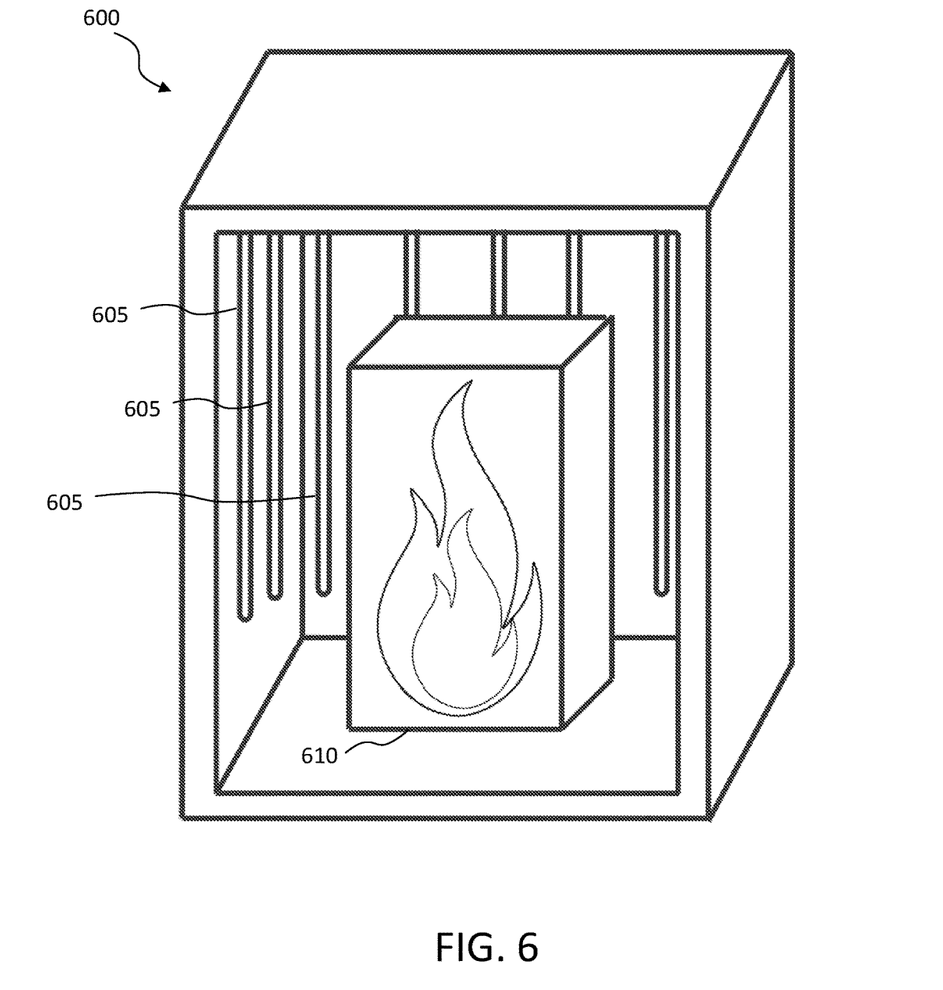
FIG. 6 shows a recharging and/or excitation station of the calibration target according to one embodiment of the disclosure.

FIG. 6 shows a recharging and/or excitation station 600 of the calibration target 610 according to one embodiment of the disclosure.

In one embodiment, when the light-emitting substance of the calibration target 610 is phosphorescence substance, the station 600 is a recharging station. The station 600 includes light sources 605 that can emit appropriate recharging light, e.g., UV ray, to recharge the energy of the phosphorescence substance contained in the target 610. After the calibration target 610 is used for a period of time, the energy stored in the phosphorescence substance are depleted and the intensity of the light emitted are reduced. The station 600 can be used to recharge the energy of the phosphorescence substance and reestablish the intensity of the light emitted by the phosphorescence substances contained in the target 610.

In one embodiment, when the light-emitting substance of the calibration target 610 is fluorescence substance, the station 600 is an excitation station. The station 600 includes light sources 605 that can emit appropriate light, e.g., UV ray, to excite the fluorescence substance contained in the target 610. The station 600 may be used to excite the calibration target 610. The station 600 may be used concurrently in combination with examples 200 and 400. When used in combination with examples 200 and 400, appropriate filters 235, 236, 237, 238, 435, 436, 437, 438 can be used to filter out the background UV ray and capture the light emitted from the area of interest of the calibration target 610 by the cameras 205, 206, 207, 208, 405, 406, 407, 408.

Figure 7:
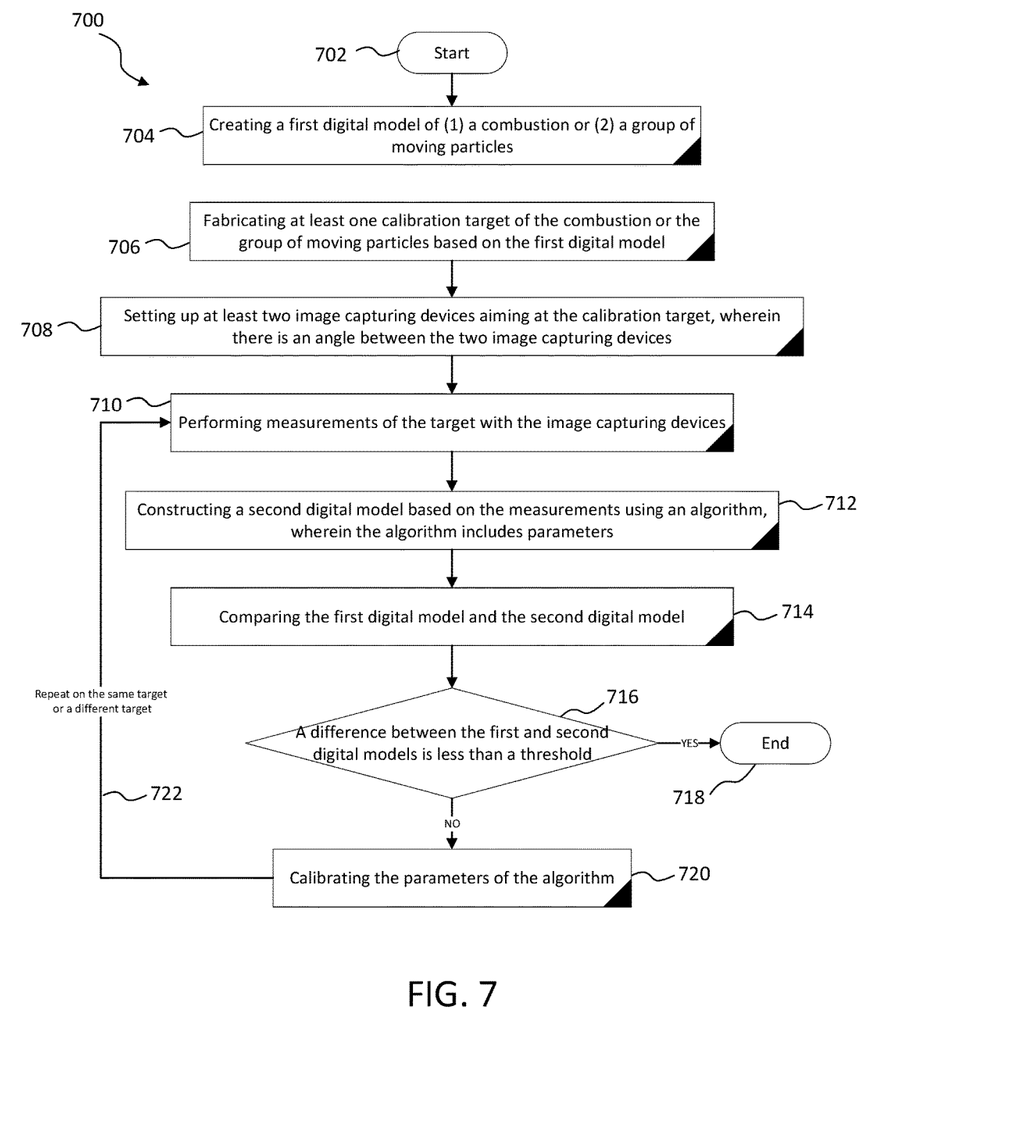
FIG. 7 shows a method of calibrating a combustion and/or moving particles model according to one embodiment of the disclosure.

FIG. 7 shows a method 700 of calibrating a combustion and/or moving particles model according to one embodiment of the disclosure. The method 700 starts at 702.

The method 700 proceeds to 704. Step 704 includes creating a first digital model of (1) a combustion or (2) a group of moving particles. In one embodiment, the first digital model is designed with known parameters for optical calibration purposes. The parameters may include fuel injection timing, shape of fuel spraying, quantity of fuel injection, ignition location, ignition timing, flame propagation, fuel burning efficiency, energy transfer efficiency, efficiency of the mixing of fuel particles, combustion chemistry, fuel burning efficiency, etc.

The method 700 proceeds to 706. Step 706 includes fabricating at least one calibration target of (1) the combustion or (2) the group of moving particles based on the first digital model. In the case of modeling the group of moving particles, it is preferred to fabricate at least two calibration targets representing different time points.

The method 700 proceeds to 708. Step 708 includes setting up at least two image capturing devices aiming at the calibration target, wherein there is an angle between the two image capturing devices. In one embodiment, the image capturing devices are cameras. In one embodiment, the cameras include optical filters.

The method 700 proceeds to 710. Step 710 includes performing measurements of the target with the imaging devices. In one embodiment, the performing measurement is capturing images and/or videos of the calibration target.

The method proceeds to 712. Step 712 includes constructing a second digital model based on the measurements (performed by the image capturing devices) using an algorithm, wherein the algorithm includes parameters. The parameters may include fuel injection timing, shape of fuel spraying, quantity of fuel injection, ignition location, ignition timing, flame propagation, fuel burning efficiency, energy transfer efficiency, efficiency of the mixing of fuel particles, fuel burning efficiency, etc.

The method proceeds to 714. Step 714 includes comparing the first digital model and the second digital model. In one embodiment, step 714 includes comparing the parameters of the first and second digital models.

The method 700 proceeds to 716. Step 716 determines whether a difference between the first and second digital models is less than a threshold. In one embodiment, step 716 includes comparing corresponding parameters in the first model and the second model. In one embodiment, the threshold is a predetermined allowable tolerance or error. In one embodiment, step 716 including determining the differences of the parameters of the first and the second digital models.

The method 700 proceeds to 718, if the determination at 716 is "YES." This means the differences between the parameters of the first digital model and the second digital model are within an acceptable range and the calibration process is completed.

The method 700 proceeds to 720, if the determination at 720 is "NO." Step 720 includes calibrating the parameters of the algorithm. In one embodiment, the parameters of the algorithm should be calibrated to make the second digital model as close to the first digital model as possible.

The method 700 proceeds to 722. Step 722 repeats the calibration process by going back to 710.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

ASPECTS

1. An apparatus for optical calibration, comprising
   a calibration target simulating a combustion, the calibration target further including
   a first light-emitting pattern; and
   a first light-emitting mechanism effecting the first light-emitting pattern; and
   two optical cameras aiming at the calibration target, wherein each optical camera has an observation axis, there is an angle between the two observation axes.
2. The apparatus according to Aspect 1, wherein the light-emitting mechanism is fluorescence.
3. The apparatus according to Aspects 1-2, wherein the light-emitting mechanism is phosphorescence.
4. The apparatus according to Aspects 1-3, wherein the light-emitting mechanism is an electricity-driven light source disposed inside of the calibration target.
5. The apparatus according to Aspects 1-4, wherein the calibration target further including a second-light emitting pattern; and
a second light-emitting mechanism effecting the second light-emitting pattern.
6. The apparatus according to Aspects 1-5, wherein at least one of the two optical cameras includes an optical filter.
7. An apparatus for optical calibration, comprising
a first calibration target simulating moving particles, the first calibration target further including
a first plurality of light-emitting particles, wherein each particle has a position at a first time (T1); and
a first light-emitting mechanism effecting the first plurality of light-emitting particles; and
two optical cameras aiming at the calibration target, wherein each optical camera has an observation axis, there is an angle between the two observation axes.
8. The apparatus according to Aspect 7, wherein the first light-emitting mechanism is fluorescence.
9. The apparatus according to Aspects 7-8, wherein the first light-emitting mechanism is phosphorescence.
10. The apparatus according to Aspects 7-9, wherein the first light-emitting mechanism is an electricity-driven light source disposed inside of the first calibration target.
11. The apparatus according to Aspects 7-10, further including
a second calibration target simulating moving particles, the second calibration target further including
a second plurality of light-emitting particles, wherein each particle has a position at a second time (T2), T2 is later than T1; and
a second light-emitting mechanism effecting the second plurality of light-emitting particles.
12. The apparatus according to Aspects 7-11, wherein at least one of the two optical cameras includes an optical filter.
13. A method for optical calibration, comprising
creating a first digital model of a combustion, wherein the first digital model includes a first parameter;
fabricating a calibration target of the combustion based on the first digital model;
setting up at least two image capturing devices aiming at the calibration target;
performing measurements of the calibration target using the at least two image capturing devices; and
constructing a second digital model based on the measurements using an algorithm, wherein the second digital model includes a second parameter.
14. The method according to Aspect 13, further comprising
comparing the first parameter and the second parameter; and
determining whether a difference between the first parameter and the second parameter is less than a threshold.
15. The method according to Aspects 13-14, further comprising
calibrating the second parameter, if the difference between the first parameter and the second parameter is not less than the threshold.
16. The method according to Aspects 13-15, wherein the first parameter is one selected from the following: fuel injection timing, shape of fuel spraying, quantity of fuel injection, ignition location, ignition timing, flame propagation, fuel burning efficiency, energy transfer efficiency, efficiency of the mixing of fuel particles, and combustion chemistry.
17. The method according to Aspects 13-16, wherein the calibration target further includes a first light-emitting pattern; and a first light-emitting mechanism effecting the first light-emitting pattern.
18. The method according to Aspects 13-17, wherein the first light-emitting mechanism is one selected form the following: fluorescence, phosphorescence, and electricity-driven light source.
19. The method according to Aspects 13-18, wherein the calibration target further includes
a second light-emitting pattern; and
a second light-emitting mechanism effecting the second light-emitting pattern.
20. The method according to Aspects 13-19, wherein the image capturing devices are cameras.

What is claimed is:
1. An apparatus for optical calibration, comprising
a first calibration target simulating a combustion, the first calibration target further including
a first light-emitting pattern;
a first light-emitting mechanism effecting the first light-emitting pattern; and
a second calibration target simulating the combustion, the second calibration target further including
a second light-emitting pattern, the second light-emitting pattern being different from the first light-emitting pattern; and
a second light-emitting mechanism effecting the second light-emitting pattern,
wherein two optical cameras image the first calibration target at a position at a first image time, the two optical cameras image the second calibration target at the position at a second image time, each optical camera has an observation axis, there is an angle between the two observation axes,
wherein the first and second calibration targets are three-dimensional physical and static objects.
2. The apparatus according to claim 1, wherein the first and/or second light-emitting mechanism is fluorescence.
3. The apparatus according to claim 1, wherein the first and/or second light-emitting mechanism is phosphorescence.
4. The apparatus according to claim 1, wherein the first and/or second light-emitting mechanism is an electricity-driven light source disposed inside of the calibration target.
5. The apparatus according to claim 1, wherein at least one of the two optical cameras includes an optical filter.
6. An apparatus for optical calibration, comprising
a first calibration target simulating moving particles, the first calibration target further including
a first plurality of light-emitting particles, wherein the first plurality of light-emitting particles have a first position at a first time (T1); and
a first light-emitting mechanism effecting the first plurality of light-emitting particles; and
a second calibration target simulating moving particles, the second calibration target further including
a second plurality of light-emitting particles, wherein the second plurality of light-emitting particles have a second position at a second time (T2), T2 is later than T1; and
a second light-emitting mechanism effecting the second plurality of light-emitting particles,
wherein two optical cameras image the first calibration target at a position at a first image time, the two optical cameras image the second calibration target at the position a second image time wherein each optical camera has an observation axis, there is an angle between the two observation axes,
wherein the first and second calibration targets are three-dimensional physical and static objects.

7. The apparatus according to claim 6, wherein the first and/or second light-emitting mechanism is fluorescence.

8. The apparatus according to claim 6, wherein the first and/or second light-emitting mechanism is phosphorescence.

9. The apparatus according to claim 6, wherein the first and/or second light-emitting mechanism is an electricity-driven light source disposed inside of the first calibration target.

10. The apparatus according to claim 6, wherein at least one of the two optical cameras includes an optical filter.

11. A method for optical calibration, comprising
creating a first digital model of a combustion, wherein the first digital model includes a first parameter;
fabricating a calibration target of the combustion based on the first digital model, wherein the calibration target is a three-dimensional physical and static object;
setting up at least two image capturing devices aiming at the calibration target;
performing measurements of the calibration target using the at least two image capturing devices; and
constructing a second digital model of the combustion based on the measurements using an algorithm, wherein the second digital model includes a second parameter;
comparing the first parameter and the second parameter;
determining whether a difference between the first parameter and the second parameter is less than a threshold; and
calibrating the second parameter, if the difference between the first parameter and the second parameter is not less than the threshold.

12. The method according to claim 11, wherein the first parameter is one selected from the following: fuel injection timing, shape of fuel spraying, quantity of fuel injection, ignition location, ignition timing, flame propagation, fuel burning efficiency, energy transfer efficiency, efficiency of the mixing of fuel particles, and combustion chemistry.

13. The method according to claim 11, wherein the calibration target further includes
a first light-emitting pattern; and
a first light-emitting mechanism effecting the first light-emitting pattern.

14. The method according to claim 13, wherein the first light-emitting mechanism is one selected form the following: fluorescence, phosphorescence, and electricity-driven light source.

15. The method according to claim 13, wherein the calibration target further includes
a second light-emitting pattern; and
a second light-emitting mechanism effecting the second light-emitting pattern.

16. The method according to claim 11, wherein the image capturing devices are cameras.

* * * * *